(12) United States Patent
Okuda

(10) Patent No.: US 9,192,311 B2
(45) Date of Patent: Nov. 24, 2015

(54) PULSE WAVE DETECTION DEVICE AND PULSE WAVE DETECTION METHOD

(75) Inventor: Noriaki Okuda, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 749 days.

(21) Appl. No.: 13/444,974

(22) Filed: Apr. 12, 2012

(65) Prior Publication Data

US 2012/0197140 A1 Aug. 2, 2012

Related U.S. Application Data

(63) Continuation of application No. PCT/JP2010/004524, filed on Jul. 13, 2010.

(30) Foreign Application Priority Data

Oct. 19, 2009 (JP) ................................. 2009-240291

(51) Int. Cl.
*A61B 5/02* (2006.01)
*A61B 5/0245* (2006.01)
*A61B 5/00* (2006.01)

(52) U.S. Cl.
CPC ........... *A61B 5/0245* (2013.01); *A61B 5/02007* (2013.01); *A61B 5/681* (2013.01); *A61B 5/6816* (2013.01); *A61B 5/6822* (2013.01); *A61B 5/6826* (2013.01); *A61B 5/6829* (2013.01); *A61B 5/6838* (2013.01); *A61B 2562/0247* (2013.01)

(58) Field of Classification Search
CPC ............................. A61B 5/024; A61B 5/02416

USPC ......................................................... 600/500
See application file for complete search history.

(56) References Cited

U.S. PATENT DOCUMENTS

| 3,953,803 | A | * | 4/1976 | Gallant et al. ............. 324/76.11 |
| 4,679,144 | A | * | 7/1987 | Cox et al. ...................... 600/516 |
| 2007/0123797 | A1 | | 5/2007 | Krause |
| 2009/0171148 | A1 | * | 7/2009 | Lu et al. ........................ 600/109 |

FOREIGN PATENT DOCUMENTS

| JP | 2001-070265 A | 3/2001 |
| JP | 2001-198094 A | 7/2001 |

(Continued)

OTHER PUBLICATIONS

PCT/JP2010/004524 Written Opinion dated Oct. 8, 2012.

*Primary Examiner* — Etsub Berhanu
(74) *Attorney, Agent, or Firm* — Arent Fox LLP

(57) ABSTRACT

A pulse wave detection device that includes a piezoelectric transducer acquiring the velocity pulse wave of a test subject and an information processing unit that processes the acquired velocity pulse wave and selectively detects regular velocity pulse wave data. The information processing unit acquires a differential waveform, extracts the extreme value of the velocity pulse wave, calculates the area value of a domain surrounded by the differential waveform and a reference line, compares the previous value and the current value of the extreme value with each other with respect to the velocity pulse waves chronologically adjacent to each other when the area value is greater than or equal to a predetermined value, and determines that the two velocity pulse waves are regular velocity pulse wave data when a difference between the two extreme values is less than or equal to a predetermined value.

14 Claims, 6 Drawing Sheets

(56) References Cited

FOREIGN PATENT DOCUMENTS

| JP | 2004-261390 A | 9/2004 |
| JP | 2007-125366 A | 5/2007 |
| JP | 2007-128366 A | 5/2007 |
| JP | 2008-253579 A | 10/2008 |

\* cited by examiner

PULSE WAVE DETECTION DEVICE AND PULSE WAVE DETECTION METHOD

CROSS REFERENCE TO RELATED APPLICATIONS

The present application is a continuation of International application No. PCT/JP2010/004524, filed Jul. 13, 2010, which claims priority to Japanese Patent Application No. 2009-240291, filed Oct. 19, 2009, the entire contents of each of which are incorporated herein by reference.

FIELD OF THE INVENTION

The present invention relates to a pulse wave detection device and a pulse wave detection method, used for detecting the pulse wave of a living body.

BACKGROUND OF THE INVENTION

A pulse wave, which is a time-dependent vascular conduction wave generated on the basis of changes in intra-arterial pressure in a living body, includes a lot of information relating to vascular dynamics ranging from a center (heart) to a periphery. Therefore, by understanding the feature of the waveform of the pulse wave of a test subject (living body), it is possible to diagnose how the heart of the test subject pumps, the behavior of a blood vessel, the state of a vascular wall, and the like, for example, and the feature of the pulse wave is used for the diagnosis of a heart disease and a peripheral arterial disease. For example, there has been known a technique in which the pulse wave of a test subject is acquired and subjected to second order differential and the vascular age of the test subject is estimated from an acquired acceleration pulse wave.

In addition, in PTL 1 described below, there has been disclosed a technique where, in a pulse wave data analysis system in which a pulse wave p-p interval is extracted from the pulse wave data of a test subject, a notch portion included in the pulse wave data is appropriately removed and a peak and a bottom are correctly detected. In this technique, first, from pulse wave data obtained by continuously measuring a pulse wave during a predetermined time, a bottom value and a peak value are sequentially detected along a temporal axis, and a bottom value and a peak value, adjacent to each other on the temporal axis, are regarded as a pair. In addition, a bottom-to-peak amplitude value, which is a difference between the bottom value and the peak value of each pair, is obtained. Next, as for the obtained bottom-to-peak amplitude value, a first amplitude value and a second amplitude value, which occur in succession on the temporal axis, are compared with each other, and when the relative value of the second amplitude value with respect to the first amplitude value is smaller than a predetermined threshold value, a bottom value and a peak value relating to the second amplitude value are temporarily deleted. In addition, furthermore, a third amplitude value existing posterior to the second amplitude value is compared with the second amplitude value, and when a relative value between the two is smaller than a predetermined threshold value, the bottom value and the peak value relating to the second amplitude value are regarded as noises and finally deleted. According to this technique, even if a respiratory amplitude fluctuation or an amplitude or the like derived from a body motion or the like exists in a pulse wave waveform, it is possible to adequately remove only a noise without deleting an intrinsic bottom value and an intrinsic peak value of the pulse wave.

PTL 1: Japanese Unexamined Patent Application Publication No. 2008-253579

SUMMARY OF THE INVENTION

Incidentally, the waveform of a pulse wave periodically occurring is not constant but fluctuates every beat. Namely, as described above, the pulse wave waveform includes the respiratory amplitude fluctuation or the amplitude or the like derived from the body motion or the like. In addition, depending on a position to which or how a pulse wave sensor for measuring the pulse wave is applied, the waveform of the acquired pulse wave also changes. Therefore, from among the acquired pulse waves, a pulse wave also exists that does not fully include a feature quantity (for example, the reflection amplitude intensity of the pulse wave or the like) used for analyzing biological information such as how a heart pumps, the behavior of a blood vessel, the state of a vascular wall, and the like.

Here, according to the technique described in PTL 1, it is possible to correctly extract the peak and the bottom of a pulse wave waveform. However, this technique performs processing for extracting peaks and bottoms with respect to all pulse wave waveforms acquired chronologically. Accordingly, in the technique described in PTL 1, a desired feature quantity is not fully included in acquired pulse wave data, namely, it is inevitable that pulse wave data ill-suited for the analysis of the biological information is included in the acquired pulse wave data. As a result, when, using the pulse wave data acquired on the basis of the technique described in PTL 1, the estimation of a vascular age or the like is performed, for example, a greatly deviated estimation result may occur.

In order to solve the above-mentioned problem point, the present invention is made and an object thereof is to provide a pulse wave detection device and a pulse wave detection method, capable of stably acquiring only a pulse wave fully including a feature quantity used for analyzing biological information.

A pulse wave detection device according to the present invention includes pulse wave acquisition means configured to acquire a pulse wave of a living body, velocity pulse wave acquisition means configured to obtain a velocity pulse wave from the pulse wave acquired by the pulse wave acquisition means, extreme value extraction means configured to extract an extreme value of the velocity pulse wave acquired by the velocity pulse wave acquisition means, and determination means configured to compare a previous extreme value and a current extreme value with each other with respect to velocity pulse waves chronologically adjacent to each other and determine that the individual velocity pulse waves including the two extreme values are regular velocity pulse waves, when a difference between the two extreme values is less than or equal to a predetermined value.

In addition, a pulse wave detection method according to the present invention includes a pulse wave acquisition step of acquiring a pulse wave of a living body, a velocity pulse wave acquisition step of obtaining a velocity pulse wave from the pulse wave acquired in the pulse wave acquisition step, an extreme value extraction step of extracting an extreme value of the velocity pulse wave acquired in the velocity pulse wave acquisition step, and a determination step of comparing a previous extreme value stored in a storing step and a current extreme value extracted in the extreme value extraction step with each other with respect to velocity pulse waves chronologically adjacent to each other and determining that the individual velocity pulse waves including the two extreme values are regular velocity pulse waves, when a difference between the two extreme values is less than or equal to a predetermined value.

According to the pulse wave detection device or the pulse wave detection method according to the present invention, with respect to the velocity pulse waves chronologically adjacent to each other, the extreme value (a peak or a bottom) of a previous velocity pulse wave and the extreme value of a subsequent velocity pulse wave are compared with each other, and when a difference between the two extreme values is less than or equal to the predetermined value, the individual extreme values are determined as regular data. Namely, when the extreme values of the velocity pulse wave waveforms occurring in succession approximately coincide with each other, the individual velocity pulse waves are determined as regular data. Therefore, it is possible to selectively detect only a velocity pulse wave (pulse wave) where an extreme value in which a feature quantity used for analyzing biological information is expressed is clear. Accordingly, it is possible to acquire a pulse wave including a feature quantity used for analyzing the biological information, namely, a pulse wave suitable for analyzing the biological information.

In the pulse wave detection device according to the present invention, it is desirable that the extreme value extraction means chronologically extracts a plurality of extreme values included in a velocity pulse wave of one beat and the determination means compares a previous value and a current value with each other with respect to each of the plural extreme values chronologically extracted and determines that the individual velocity pulse waves including two extreme values are regular velocity pulse waves, when a difference between the two extreme values is less than or equal to a predetermined value with respect to every extreme value.

In addition, in the pulse wave detection method according to the present invention, it is desirable that, in the extreme value extraction step, a plurality of extreme values included in a velocity pulse wave of one beat are chronologically extracted and in the determination step, a previous value and a current value are compared with each other with respect to each of the plural extreme values chronologically extracted and it is determined that the individual velocity pulse waves including two extreme values are regular velocity pulse waves, when a difference between the two extreme values is less than or equal to a predetermined value with respect to every extreme value.

In this case, with respect to velocity pulse waves chronologically adjacent to each other, a plurality of extreme values of a previous velocity pulse wave are compared with a plurality of extreme values of a subsequent velocity pulse wave, and when a difference between two extreme values is less than or equal to the predetermined value with respect to every extreme value, the individual velocity pulse waves are determined as the regular data. Namely, when the plural extreme values of one velocity pulse wave waveform approximately coincide with the plural extreme values of the other velocity pulse wave waveform, respectively, the velocity pulse wave waveforms occurring in succession, the velocity pulse waves are determined as regular data. Therefore, it is possible to select and detect only a velocity pulse wave where all of the plural extreme values (for example, third, fourth, and fifth extreme values in time series order) in which a feature quantity used for analyzing biological information is expressed are clear. Accordingly, it is possible to stably acquire only a pulse wave fully including a feature quantity used for analyzing the biological information.

In the pulse wave detection device according to the present invention, it is desirable that the extreme value extraction means extract an extreme value with respect to each of velocity pulse waves corresponding to three beats or more and the determination means compares the extreme values with each other with respect to the velocity pulse waves corresponding to three beats or more and determines that the above-mentioned velocity pulse waves corresponding to three beats or more are regular velocity pulse waves, when a difference between the extreme values is less than or equal to a predetermined value a plurality of successive times.

In addition, in the pulse wave detection method according to the present invention, it is desirable that in the extreme value extraction step, an extreme value is extracted with respect to each of velocity pulse waves corresponding to three beats or more and in the determination step, the extreme values are compared with each other with respect to the velocity pulse waves corresponding to three beats or more and it is determined that the above-mentioned velocity pulse waves corresponding to three beats or more are regular velocity pulse waves, when a difference between the extreme values is less than or equal to a predetermined value a plurality of successive times.

In this case, when all of the extreme values of each of the velocity pulse wave waveforms that chronologically line and correspond to three beats (three waves) or more approximately coincide, each of the velocity pulse waves is determined as regular data. Therefore, it is possible to more certainly select and detect a velocity pulse wave where an extreme value in which a feature quantity used for analyzing biological information is expressed is clear. Accordingly, it is possible to stably acquire only a pulse wave fully including a feature quantity used for analyzing the biological information.

In the pulse wave detection device according to the present invention, it is desirable that when, from among a plurality of extreme values included in a velocity pulse wave of one beat, a difference between an earliest extreme value and a final extreme value falls within a predetermined time, the determination means determines that the velocity pulse wave is a regular velocity pulse wave.

In addition, in the pulse wave detection method according to the present invention, it is desirable that, in the determination step, when, from among a plurality of extreme values included in a velocity pulse wave of one beat, a difference between an earliest extreme value and a final extreme value falls within a predetermined time, it is determined that the velocity pulse wave is a regular velocity pulse wave.

In such a way, it is possible to effectively remove a velocity pulse wave where the difference between the earliest extreme value and the final extreme value does not fall within the predetermined time, for example, a velocity pulse wave out of shape.

It is desirable that the pulse wave detection device according to the present invention further includes differential waveform acquisition means configured to subject the velocity pulse wave acquired by the velocity pulse wave acquisition means to differential processing and acquire a differential waveform and area value calculation means configured to obtain an area value of a domain surrounded by the differential waveform acquired by the differential waveform acquisition means and a reference line, wherein the determination means performs the comparison of an extreme value when the area value obtained by the area value calculation means is greater than or equal to a predetermined value.

In addition, it is desirable that the pulse wave detection method according to the present invention further includes a differential waveform acquisition step of subjecting the velocity pulse wave acquired in the velocity pulse wave acquisition step to differential processing and acquiring a differential waveform and an area value calculation step of obtaining an area value of a domain surrounded by the differential waveform acquired in the differential waveform acquisition step and a reference line, wherein in the determination step, the comparison of an extreme value is performed when the area value obtained in the area value calculation step is greater than or equal to a predetermined value.

In this case, the size of an area surrounded by the differential waveform and the reference line exceeds the predetermined value, namely, the amplitude of the velocity pulse wave to be subjected to differential processing is greater than or equal to a predetermined level, the comparison of the extreme value is performed. Accordingly, after separating the velocity pulse wave with a large amplitude from the velocity pulse wave with a small amplitude, it is possible to perform the comparison of the extreme value. Therefore, it is possible to selectively extract only a velocity pulse wave where an extreme value in which a feature quantity used for analyzing the biological information is expressed is large and clear. In addition, in this case, since the extreme value of the velocity pulse wave is compared on the basis of a time point when the area value exceeds the predetermined value, it is possible to unify extreme values to be targets for comparison.

It is desirable that the pulse wave detection device according to the present invention further includes number-of-pulses calculation means configured to calculate the number of pulses of the living body on the basis of a period when the area value acquired by the area value calculation means has a maximum value.

In addition, it is desirable that the pulse wave detection method according to the present invention further includes a number-of-pulses calculation step of calculating the number of pulses of the living body on the basis of a period when the area value acquired in the area value calculation step has a maximum value.

In such a way, it is possible to calculate the number of pulses of the living body from the period when the area value has a maximum value. Accordingly, when the regular data of the velocity pulse wave is detected, in conjunction therewith, it is possible to acquire the number of pulses of the living body. In addition, since the number of pulses is calculated from the pulse wave waveform whose extreme value is clear, it is possible to obtain the more correct number of pulses.

In the pulse wave detection device according to the present invention, it is desirable that a piezoelectric transducer is used as the pulse wave acquisition means. In the pulse wave detection method according to the present invention, it is desirable that, in the pulse wave acquisition step, the pulse wave of the living body is acquired using a piezoelectric transducer.

In this case, since, by only applying the piezoelectric transducer to the skin surface of the living body (test subject), it is possible to detect the pulse wave, it is possible to detect the pulse wave simply and with no injury and no pain.

According to the present invention, it is possible to stably acquire only a pulse wave fully including a feature quantity used for analyzing biological information.

DETAILED DESCRIPTION OF THE PREFERRED EMBODIMENTS

Hereinafter, the preferred embodiment of the present invention will be described in detail with reference to drawings. In addition, in each drawing, a same symbol will be assigned to a same element and the redundant description thereof will be omitted.

Figure 1:
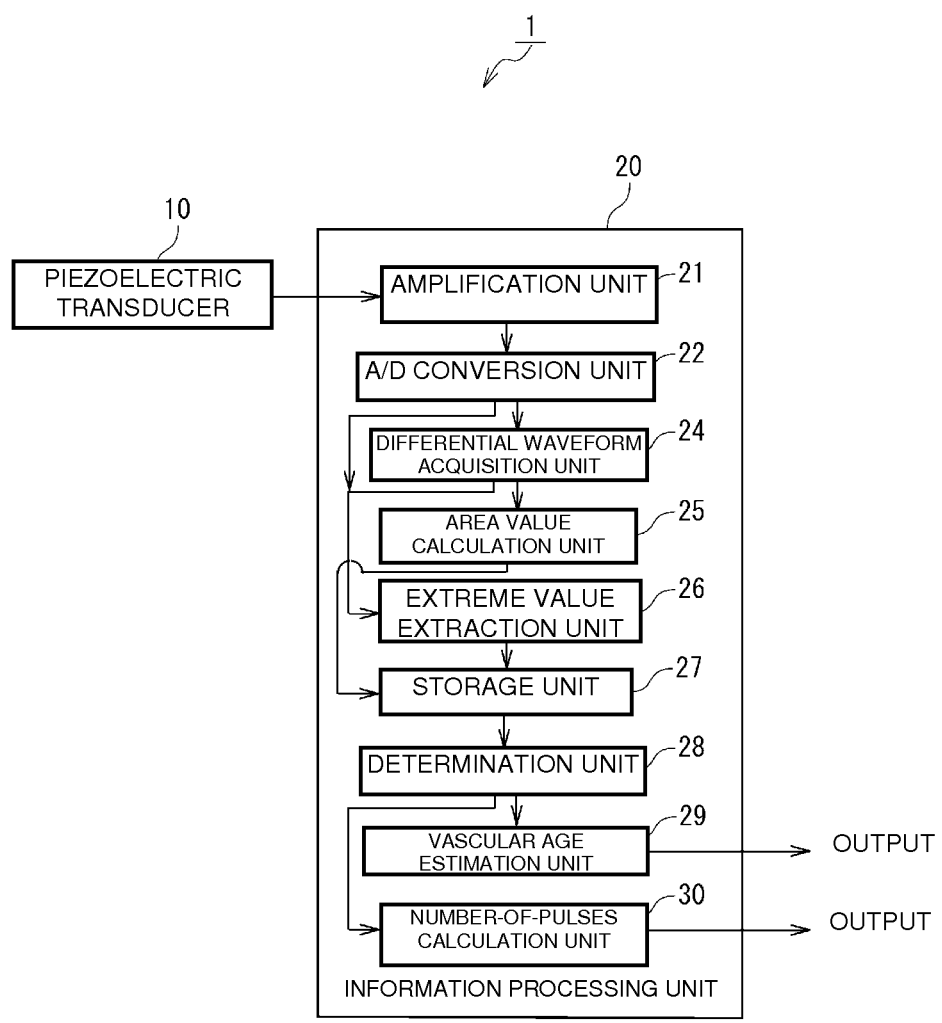
FIG. 1 is a block diagram illustrating a configuration of a pulse wave detection device according to an embodiment.

First, using FIG. 1, the configuration of a pulse wave detection device 1 according to the embodiment will be described. FIG. 1 is a block diagram illustrating the configuration of the pulse wave detection device 1.

The pulse wave detection device 1 stably detects only a velocity pulse wave (pulse wave) that fully includes a feature quantity used for analyzing biological information and is suitable for the analysis of the biological information. In addition, the pulse wave detection device 1 also includes a function for measuring the number of pulses of a test subject and a function for estimating a vascular age, using the detected velocity pulse wave. Therefore, the pulse wave detection device 1 includes a piezoelectric transducer 10 acquiring the velocity pulse wave of the test subject and an information processing unit 20 that selectively detects, from the acquired velocity pulse waves, a velocity pulse wave including a feature quantity used for analyzing the biological information and obtains the number of pulses and the vascular age of the test subject from the detected regular velocity pulse wave. This information processing unit 20 includes an amplification unit 21, an A/D conversion unit 22, a differential waveform acquisition unit 24, an area value calculation unit 25, an extreme value extraction unit 26, a storage unit 27, a determination unit 28, a vascular age estimation unit 29, and a number-of-pulses calculation unit 30. Hereinafter, each configuration will be described in detail.

The piezoelectric transducer 10 is a sensor that converts a pulse wave propagating through the artery of the test subject into a velocity signal. Namely, the piezoelectric transducer 10 functions as pulse wave acquisition means and velocity pulse wave acquisition means. Here, while it is possible for the piezoelectric transducer 10 to detect the pulse wave as any one of the velocity signal and a displacement signal, it is desirable for the piezoelectric transducer 10 to detect the pulse wave as the velocity signal. In addition, in the case of a piezoelectric transducer of the displacement output, it is possible to obtain the velocity signal (velocity pulse wave) by differentiating the displacement output. In this case, the piezoelectric transducer corresponds to a pulse wave acquisition means, and a differentiator differentiating the displacement output corresponds to a velocity pulse wave acquisition means. In addition, in the case of a piezoelectric transducer of a velocity output, it is possible to obtain the displacement signal (pulse wave) by subjecting the velocity output to time integration.

Figure 2:
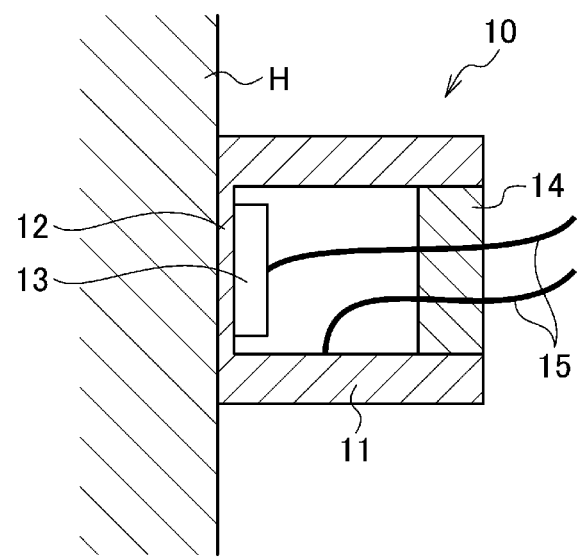
FIG. 2 is a cross-sectional view of a piezoelectric transducer used for the pulse wave detection device according to the embodiment.

Here, the cross-section of the piezoelectric transducer 10 is illustrated in FIG. 2. In the piezoelectric transducer 10, a unimorph structure is included, a flat bottom portion 12 of a bottomed cylindrical case 11 is configured as a vibrating surface, and a piezoelectric element 13 is fixed to the inner surface of that bottom portion 12. The opening portion of the case 11 is closed with a sealing material 14, and a lead wire 15 is extracted through this sealing material 14. In addition, the piezoelectric transducer 10 is not limited to the structure illustrated in FIG. 2. When the velocity pulse wave is acquired, the outer surface of the bottom portion 12 is applied to the skin of a test subject H. In addition, as a region from which the velocity pulse wave is acquired, namely, a region to which the piezoelectric transducer 10 is applied, for example, a region ranging between the wrist of the test subject H and the fingertip thereof is desirable. In this regard, however, a measurement point is not limited to the region ranging between the wrist and the fingertip, and if it is possible to measure the pulse wave of an artery from a region, the region may be any one of an ear, a cervical region, an ankle region, a femoral region, and the like. The piezoelectric transducer 10 is connected to the information processing unit 20 through the lead wire 15 and a wiring line, and an acquired velocity pulse wave signal is output to the information processing unit 20.

The information processing unit 20 extracts the extreme values (peak and bottom) of the velocity pulse wave acquired by the piezoelectric transducer 10 and compares the extreme values with each other with respect to a plurality of chronologically successive velocity pulse waves where the area values of the waveforms thereof subjected to differential processing are greater than or equal to a predetermined value. In addition, when a difference between the extreme values falls within a predetermined value a plurality of successive times, the information processing unit 20 detects a velocity pulse wave including the extreme value, as regular velocity pulse wave data. Accordingly, the information processing unit 20 selectively detects only a velocity pulse wave where an extreme value in which a feature quantity used for analyzing the biological information is expressed is large and clear. In addition, as described above, the information processing unit 20 also includes the function for measuring the number of pulses of the test subject and the function for estimating a vascular age, using the detected regular velocity pulse wave.

The information processing unit 20 includes the amplification unit 21 serving as an input interface, the A/D conversion unit 22, a CPU performing arithmetic processing on a velocity pulse wave input through the amplification unit 21 and the A/D conversion unit 22, a ROM storing therein a program causing the CPU to execute each processing and data, a RAM temporarily storing therein various kinds of data such as a calculation result and the like, a backup RAM backing up thereinto data, and the like. In the information processing unit 20, the program stored in the ROM is executed by the CPU, and hence the functions of the differential waveform acquisition unit 24 to the number-of-pulses calculation unit 30 are realized. In addition, in place of the CPU, for example, an ASIC, an FPGA, a DSP, or the like may be used.

For example, the amplification unit 21 includes an amplifier utilizing an operational amplifier or the like, and amplifies the velocity pulse wave signal acquired by the piezoelectric transducer 10. The velocity pulse wave signal amplified in the amplification unit 21 is output to the A/D conversion unit 22. The A/D conversion unit 22 includes an A/D converter, and converts, into digital data, the velocity pulse wave signal (analog signal) detected by the piezoelectric transducer 10 and amplified in the amplification unit 21. The digital-converted velocity pulse wave is output to the differential waveform acquisition unit 24 and the extreme value extraction unit 26. In addition, as preprocessing, a configuration may be adopted in which a noise is removed from the velocity pulse wave signal using a low pass filter, a band pass filter, or the like. Alternatively, a noise may be removed by performing filtering processing using a digital filter after A/D conversion.

The differential waveform acquisition unit 24 performs differential processing on the acquired velocity pulse wave, and acquires a differential waveform. Namely, the differential waveform acquisition unit 24 functions as differential waveform acquisition means. More specifically, for example, when a sampling frequency is set to 500 Hz, a difference value (DPW) between the current value (VPW0) of the velocity pulse wave and a value (VPW1) previous thereto by 16 samplings is calculated in accordance with the following Expression (1) so as to consider the influence of a noise. In addition, this processing is sequentially repeatedly performed every sampling data, and hence the differential waveform is acquired.

$$DPW = VPW0 - VPW1 \quad (1)$$

Figure 3:
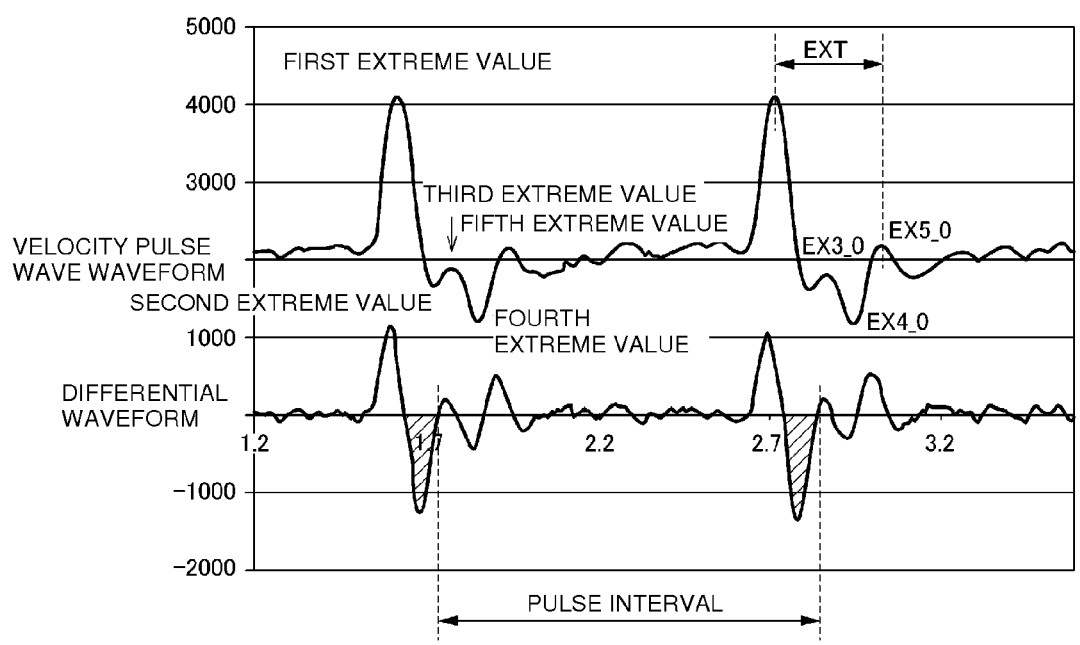
FIG. 3 is a diagram illustrating examples of a velocity pulse wave waveform of a test subject whose age is high and a differential waveform thereof.
Figure 4:
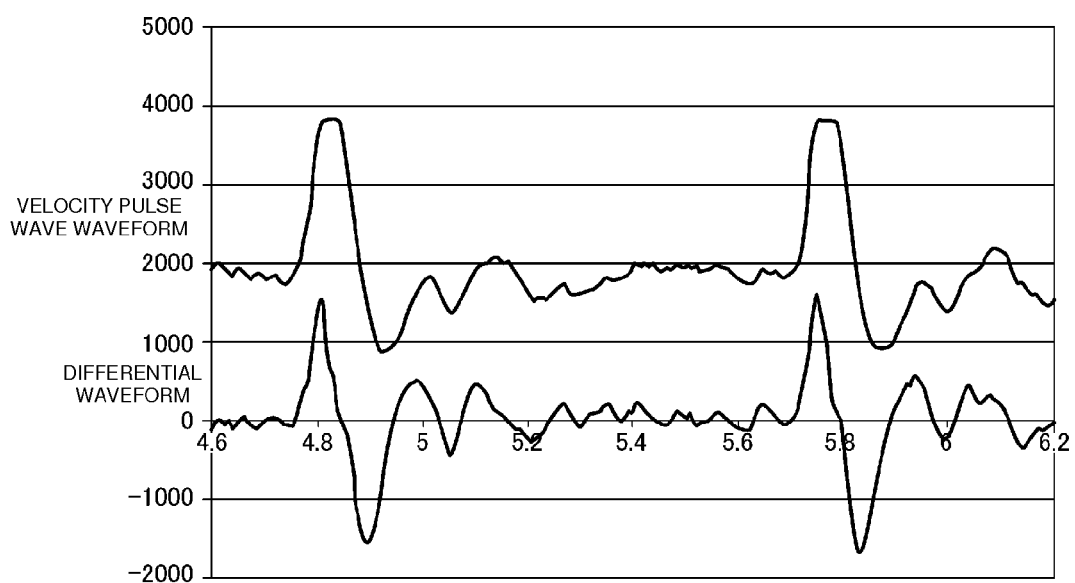
FIG. 4 is a diagram illustrating examples of a velocity pulse wave waveform of a test subject whose age is low and a differential waveform thereof.

Here, FIG. 3 illustrates examples of the velocity pulse wave waveform (on an upper side) of a test subject whose age is high (41 years old) and the differential waveform thereof (on a lower side). In addition, FIG. 4 illustrates examples of the velocity pulse wave waveform (on an upper side) of a test subject whose age is low (25 years old) and the differential waveform thereof (on a lower side). In addition, the differential waveform acquired by the differential waveform acquisition unit 24 is output to the extreme value extraction unit 26 and the area value calculation unit 25.

Every one beat (one wave), the extreme value extraction unit 26 chronologically extracts a plurality of extreme values included in the velocity pulse wave. Namely, the extreme value extraction unit 26 functions as extreme value extraction means. In addition, in the present embodiment, as illustrated in FIG. 3, five extreme values (a first extreme value EX1 to a fifth extreme value EX5) are extracted. More specifically, first, the extreme value extraction unit 26 detects a point at which the difference value DPW calculated in accordance with the Expression (1) switches from a positive to a negative or switches from a negative to a positive. Next, the extreme value extraction unit 26 extracts, as an extreme value, velocity pulse wave data VPW2 previous, by eight points (previous, by eight samplings), to a point at which the sign of the difference value DPW switches. In addition, the extreme value extraction unit 26 repeatedly performs this processing and extracts five extreme values every one beat. In addition, the extreme values (the first extreme value EX1 to the fifth extreme value EX5) of the velocity pulse wave, extracted by the extreme value extraction unit 26, are output to the storage unit 27 and the determination unit 28.

On the other hand, the area value calculation unit 25 calculates the integrated value of a domain surrounded by the differential waveform acquired by the differential waveform acquisition unit 24 and a reference line (a line where the difference value is zero), namely, the area value SDPW of the domain. Accordingly, the area value calculation unit 25 functions as area value calculation means. Here, it is assumed that the calculated area values SDPW are a first area value SDPW1, a second area value SDPW2, a third area value SDPW3, a fourth area value SDPW4, and a fifth area value SDPW5 in time series order. In addition, the individual area values SDPW1 to SDPW5 calculated by the area value calculation unit 25 are output to the storage unit 27 and the number-of-pulses calculation unit 30.

The storage unit 27 includes the above-mentioned RAM and the like, and when, from among the area values SDPW calculated by the area value calculation unit 25, the area value SDPW on a side on which the output value of the differential waveform is negative is greater than or equal to a predetermined value (threshold value), the storage unit 27 stores therein the extreme value extracted in the extreme value extraction unit 26. Here, it is assumed that five extreme values extracted by the extreme value extraction unit 26 are a first extreme value EX1, a second extreme value EX2, a third extreme value EX3, a fourth extreme value EX4, and a fifth extreme value EX5 in time series order, and when the second area value SDPW2 (refer to a hatched portion in FIG. 3) is greater than or equal to a predetermined value, the storage unit 27 continues to store therein extreme values subsequent to the second area value SDPW2, namely, the third extreme value EX3, the fourth extreme value EX4, and the fifth extreme value EX5. In addition, usually, from among the first area value SDPW1 to the fifth area value SDPW5, the second area value SDPW2 is the largest. In addition, in particular, the characteristic information of the test subject (living body) is included in the third extreme value EX3, the fourth extreme value EX4, and the fifth extreme value EX5 of the velocity pulse wave. Here, as illustrated in FIG. 3, as for the first area value SDPW1, the third area value SDPW3, and the fifth area value SDPW5, the output values of the differential waveform correspond to positive areas, and as for the second area value SDPW2 and the fourth area value SDPW4, the output values of the differential waveform correspond to negative areas. Therefore, by distinguishing whether the output value of the differential waveform is positive or negative, it is possible to exclude the first area value SDPW1, the third area value SDPW3, and the fifth area value SDPW5. Accordingly, it is desirable that the above-mentioned predetermined value is set to a value larger than the maximum value of the fourth area value SDPW4 and smaller than the second area value SDPW2. In addition, when the second area value SDPW2 is less than the predetermined value (namely, the amplitude of the velocity pulse wave is small), the data of this velocity pulse wave is discarded.

With respect to each of a plurality (for example, three) of extreme values chronologically extracted, the determination unit 28 sequentially performs, on a plurality (for example, three) of velocity pulse waves, processing for comparing a previous value with a current value. In addition, when, with respect to the plural extreme values, a difference between two extreme values has become less than or equal to a predetermined value a plurality of successive times (for example, twice), the determination unit 28 determines that each velocity pulse wave is regular velocity pulse wave data. Namely, the determination unit 28 functions as determination means.

Figure 5:
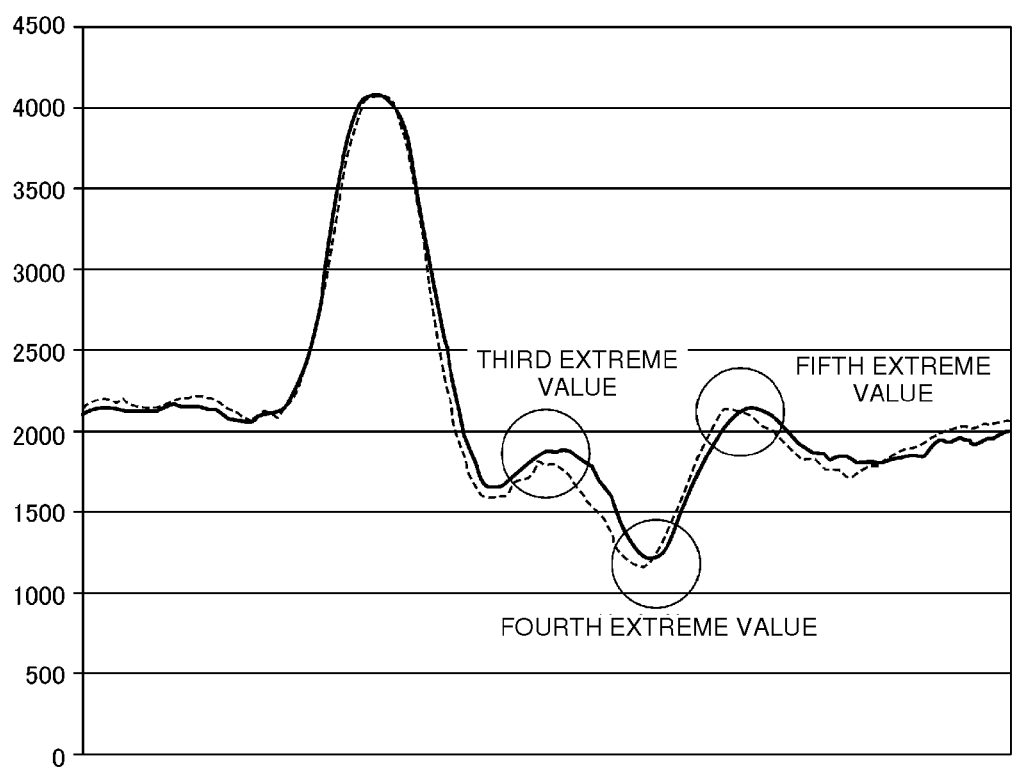
FIG. 5 is a diagram for explaining a comparison method for an extreme value of a velocity pulse wave.

More specifically, first, with respect to velocity pulse waves chronologically adjacent to each other, the determination unit 28 calculates a difference (absolute value) between the previous (preceding by one beat) third extreme value EX3_1 stored in the storage unit 27 and the current third extreme value EX3_0, a difference (absolute value) between the previous fourth extreme value EX4_1 and the current fourth extreme value EX4_0, and a difference (absolute value) between the previous fifth extreme value EX5_1 and the current fifth extreme value EX5_0 in accordance with the following Expressions (2.1) to (2.3) (refer to the insides of circles in FIG. 5: In addition, in FIG. 5, a dashed line indicates a velocity pulse wave waveform preceding by one beat).

$$DEX3 = |EX3\_0 - EX3\_1| \quad (2.1)$$

$$DEX4 = |EX4\_0 - EX4\_1| \quad (2.2)$$

$$DEX5 = |EX5\_0 - EX5\_1| \quad (2.3)$$

Next, the determination unit 28 determines whether or not each of the differences DEX3, DEX4, and DEX5 between the extreme values, calculated in accordance with the above-mentioned Expressions (2.1) to (2.3), falls within the predetermined value. In addition, the determination unit 28 sequentially executes this processing twice with respect to three velocity pulse waves, and when each difference between extreme values has become less than or equal to the predetermined value two successive times (for example, three successive waves), the determination unit 28 determines that an adequate waveform is obtained. In addition, the determination unit 28 regards the three velocity pulse waves used as targets for comparison, as regular velocity pulse wave data. On the other hand, when any one of differences between the extreme values has become larger than the predetermined value at least once, the determination unit 28 determines that an adequate waveform is not obtained, and discards the data of the corresponding velocity pulse wave. Here, in the present embodiment, the predetermined value is set to 2% of zero-span (12 bits). Namely, the predetermined value is set to 2% of 0-FFFH (0-4096)~52H (82). In addition, this predetermined value may be arbitrarily set.

Furthermore, when, from among the five extreme values included in the velocity pulse wave of one beat, a time difference EXT between the first extreme value EX1 and the fifth extreme value EX5 falls within a predetermined time, the determination unit 28 determines that the corresponding velocity pulse wave is a regular velocity pulse wave (refer to FIG. 3). On the contrary, when the time difference EXT between the first extreme value EX1 and the fifth extreme value EX5 is longer than the predetermined time, the corresponding velocity pulse wave is discarded. Accordingly, for example, a velocity pulse wave whose waveform is out of shape is removed. In addition, the regular velocity pulse wave data determined by the determination unit 28 is output to the number-of-pulses calculation unit 30 and the vascular age estimation unit 29.

The vascular age estimation unit 29 processes and analyzes the regular velocity pulse wave output from the determination unit 28 and estimates the vascular age of the test subject. Incidentally, a pressure wave propagating through the inside of a blood vessel emerges, as a displacement, on a body surface to become the pulse wave. This pulse wave includes an incident wave component, due to a forward traveling wave generated owing to the bloodstream ejection of a heart, and a reflected wave component, generated owing to the fact that the forward traveling wave propagates through the blood vessel and is reflected from a periphery (hereinafter, the individual components are referred to as an incident wave and a reflected wave). Since propagating to the periphery, the reflected wave is strongly dependent on the viscoelastic property of the vascular wall and notably changes owing to the sclerosis of the vascular wall. Accordingly, when the incident wave and the reflected wave are separated from each other and the reflected wave is evaluated, it may be considered that it is possible to determine the sclerosis state of the blood vessel.

Therefore, the vascular age estimation unit 29 integrates the regular velocity pulse wave acquired in the determination unit 28, and acquires the pulse wave. In addition to this, the vascular age estimation unit 29 decomposes the corresponding pulse wave into a plurality of expanded waveforms (the incident wave and the reflected wave). As a decomposition method, a Multi-Peak-Fitting method is used. The Multi-Peak-Fitting method is a method in which a composite waveform is decomposed into expanded waveforms using an arbitrary fitting function, and the Multi-Peak-Fitting method is used for decomposing the pulse wave into the incident wave and the reflected wave. Here, using an Exponential Gaussian function considered to be most similar to an incident waveform as the fitting function, first the incident wave has been approximated. Next, after the reflected wave has been obtained by subtracting the incident wave from the pulse wave, the obtained reflected wave has been decomposed into a plurality of expanded waveforms of the Exponential Gaussian. As the fitting function, in addition to the Exponential Gaussian function, an arbitrary nonlinear fitting function such as a Gaussian function, a Voigt function, a Log-Normal function, a Lorenz function, or the like may be selected in response to the pulse wave waveform.

Owing to utilizing the Multi-Peak-Fitting method, it is possible to decompose the pulse wave into the incident wave and the reflected wave, and it is possible to consider the pulse wave as the superposition of these waveforms. In addition, in the vascular age estimation unit 29, the reflected wave separated from the pulse wave may be further decomposed into a plurality of expanded waves. The amplitude intensities (peak intensities) of the decomposed incident wave and the decomposed reflected wave are compared with each other, and the degree of an arterial sclerosis is evaluated in accordance with the comparison result. The estimation result of the vascular age, performed by the vascular age estimation unit 29, is output to the outside through an output interface (the illustration thereof is omitted).

Using the regular velocity pulse wave acquired in the determination unit 28, the number-of-pulses calculation unit 30 calculates the number of pulses of the test subject on the basis of the period of the maximum value of the area value SDPW acquired by the area value calculation unit 25. More specifically, for example, the number-of-pulses calculation unit 30 calculates the number of pulses from a time interval at which the second area value SDPW2 having the maximum value is output. Namely, the number-of-pulses calculation unit 30 functions as number-of-pulses calculation means. In addition, the number of pulses of the test subject calculated by the number-of-pulses calculation unit 30 is output to the outside through an output interface (the illustration thereof is omitted).

Figure 6:
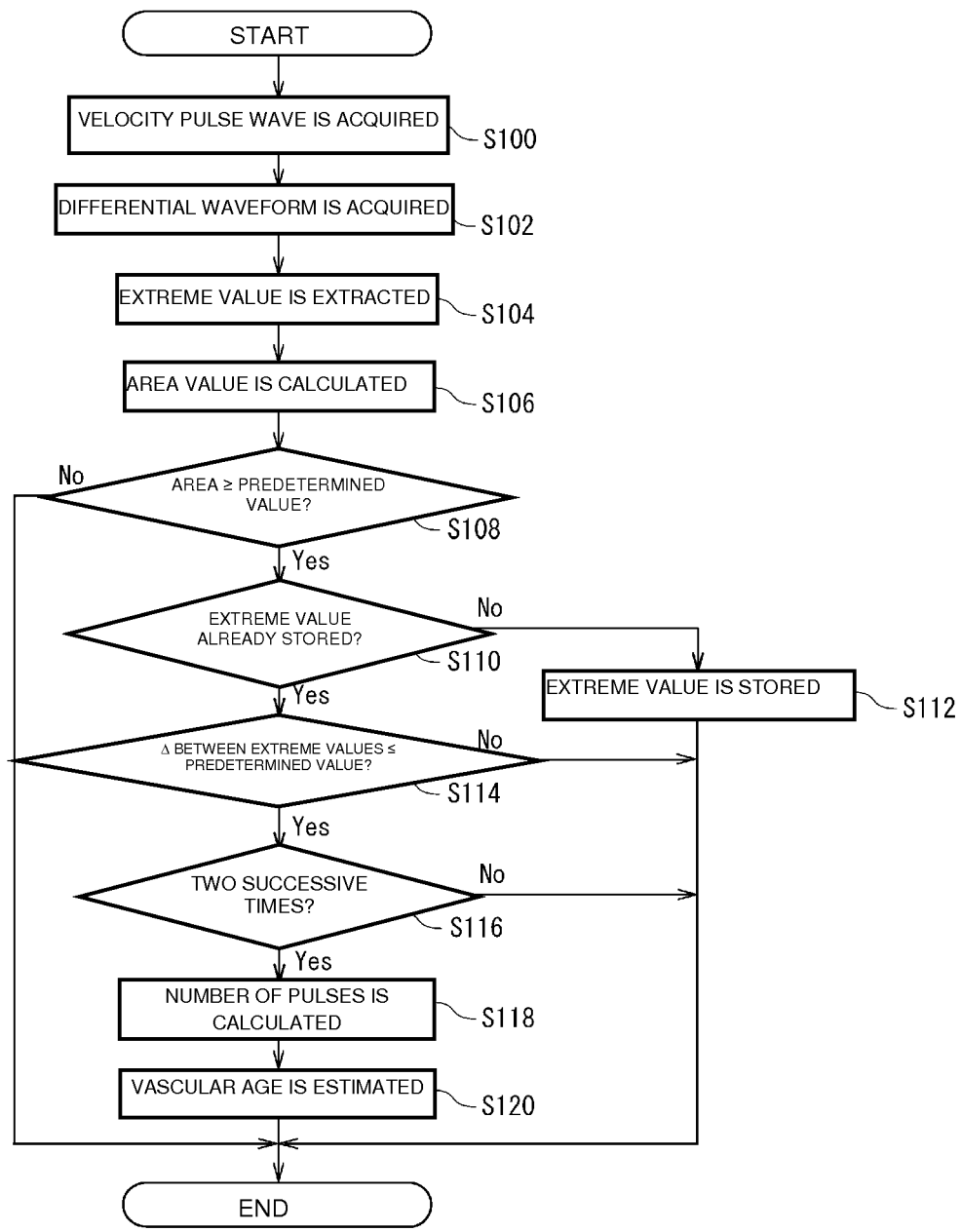
FIG. 6 is a flowchart illustrating a processing procedure of pulse wave detection processing performed by the pulse wave detection device according to the embodiment.

Next, the operation of the pulse wave detection device 1 and a pulse wave detection method will be described with reference to FIG. 6. FIG. 6 is a flowchart illustrating the processing procedure of pulse wave detection processing performed by the pulse wave detection device 1. This pulse wave detection processing is repeatedly executed with predetermined timing (for example, every 2 msec).

First, in Step S100, for example, owing to the piezoelectric transducer 10 applied to the wrist or the like of the test subject, the velocity pulse wave of the test subject is acquired. Next, in Step S102, after having been amplified and converted into digital data, the velocity pulse wave detected in Step S100 is subjected to differential processing, thereby acquiring a differential waveform. In addition, since the detail of the differential processing is as described above, the detailed description thereof will be omitted here. Subsequently, in Step S104, as for the differential waveform acquired in Step S102, a point at which the sign of a difference value switches is detected, and on the basis of that point, the five extreme values of the velocity pulse wave are extracted. In addition, here, a velocity pulse wave is discarded where the time difference EXT between the first extreme value EX1 and the fifth extreme value EX5 included in the five extracted extreme values is longer than the predetermined time.

In subsequent Step S106, the area values SDPW1 to SDPW5 of five domains surrounded by the differential waveform acquired in Step S102 and the reference line are calculated. Next, in Step S108, it is determined whether or not the second area value SDPW2 or the fourth area value SDPW4 is greater than or equal to the predetermined value, from among the area values SDPW1 to SDPW5 calculated in Step S106. Here, when either area value SDPW is greater than or equal to the predetermined value, the processing shifts to Step S110. On the other hand, when both of the area values SDPW2 and SDPW4 are less than the predetermined value, breaking out of the present processing is performed once after the velocity pulse wave data has been discarded.

When the area value SDPW of the differential waveform is greater than or equal to the predetermined value, it is determined, in Step S110, whether or not an extreme value has already been stored. Here, when the extreme value has already been stored, the processing shifts to Step S114. On the other hand, when the extreme value has not been stored yet, breaking out of the present processing is performed once after the extreme values (the third extreme value EX3, the fourth extreme value EX4, and the fifth extreme value EX5) have been stored in Step S112.

In Step S114, the current values of the three extreme values are sequentially stored, and as for each of the third extreme value EX3, the fourth extreme value EX4, and the fifth extreme value EX5, it is determined whether or not a difference between a previous value and a current value is less than or equal to the predetermined value. Here, when, as for every extreme value, a difference between a previous value and a current value is less than or equal to the predetermined value, the processing shifts to Step S116. On the other hand, when as for each of one or more extreme values, a difference between a previous value and a current value is larger than the predetermined value, breaking out of the present processing is performed once after these pieces of velocity pulse wave data have been discarded.

In Step S116, it is determined whether or not Step S114 has been affirmative two successive times (for example, with respect to three successive waves). Here, when Step S114 has been affirmative two successive times, it is determined that the compared velocity pulse wave is regular velocity pulse wave data, and the processing shifts to Step S118. On the other hand, when Step S114 has been affirmative only once, the processing shifts to Step S100, and until Step S114 has been affirmative two successive times, the above-mentioned processing in Step S100 to S116 is repeatedly executed.

In Step S118, as for the regular velocity pulse wave data, for example, from a time interval at which the second area value SDPW2 having a maximum value is output, the number of pulses is calculated. Subsequently, in Step S120, on the basis of the Multi-Peak-Fitting method, the vascular age of the test subject is estimated. In addition, since the estimation method of the vascular age is as described above, the detailed description thereof will be omitted here. After that, the present processing is terminated.

According to the present embodiment, with respect to velocity pulse waves chronologically adjacent to each other, the extreme value of a previous velocity pulse wave are compared with the extreme value of a subsequent velocity pulse wave, and when a difference between the two extreme values is less than or equal to a predetermined value, each of the velocity pulse waves is determined as regular data. Namely, when the extreme values of the velocity pulse wave waveforms occurring in succession approximately coincide with each other, each of the velocity pulse waves is determined as regular data. Therefore, it is possible to selectively detect only a velocity pulse wave (pulse wave) where extreme values (a peak and a bottom) in which a feature quantity used for analyzing biological information is expressed are clear. Accordingly, it is possible to acquire a pulse wave including a feature quantity used for analyzing the biological information, namely, a pulse wave suitable for analyzing the biological information.

In addition, according to the present embodiment, with respect to velocity pulse waves chronologically adjacent to each other, the previous value and the current value of each of the third extreme value EX3, the fourth extreme value EX4, and the fifth extreme value EX5 are compared with each other, and when, with respect to every extreme value, the difference DEX between the extreme values is less than or equal to the predetermined value, the velocity pulse wave is determined as the regular data. Namely, when the three extreme values of one velocity pulse wave waveform approximately coincide with the three extreme values of the other velocity pulse wave waveform, respectively, the velocity pulse wave waveforms occurring in succession, each of the velocity pulse waves is determined as regular data. Therefore, it is possible to select and detect only a velocity pulse wave where all of the three extreme values (the third extreme value EX3 to the fifth extreme value EX5) in which a feature quantity used for analyzing biological information is expressed are clear. Accordingly, it is possible to acquire only a pulse wave fully including a feature quantity used for analyzing the biological information, namely, a pulse wave suitable for analyzing the biological information.

In addition, according to the present embodiment, when all of the extreme values of each of the velocity pulse wave waveforms that chronologically line and correspond to three beats (three waves) or more approximately coincide, each of the velocity pulse waves is determined as regular data. Therefore, it is possible to more certainly select and detect a velocity pulse wave where an extreme value in which a feature quantity used for analyzing biological information is expressed is clear. Accordingly, it is possible to stably acquire only a pulse wave fully including a feature quantity used for analyzing the biological information, namely, a pulse wave suitable for analyzing the biological information.

Furthermore, according to the present embodiment, the size of the area SDPW surrounded by the differential waveform and the reference line exceeds a predetermined value, namely, the amplitude of the velocity pulse wave to be subjected to the differential processing is greater than or equal to a predetermined level, the extreme value is stored to be compared. Accordingly, after separating the velocity pulse wave with a large amplitude from the velocity pulse wave with a small amplitude, it is possible to perform the comparison of the extreme value. Therefore, it is possible to selectively extract only a velocity pulse wave where an extreme value in which a feature quantity used for analyzing the biological information is expressed is large and clear. In addition, in this case, since the extreme value of the velocity pulse wave is compared on the basis of a time point when the area value SDPW exceeds the predetermined value, it is possible to unify extreme values to be targets for comparison.

According to the present embodiment, when the time difference EXT between the first extreme value EX1 and the fifth extreme value EX5 is longer than the predetermined time, velocity pulse wave data is discarded. Accordingly, it is possible to effectively remove a velocity pulse wave where the time difference EXT between the first extreme value EX1 and the fifth extreme value EX5 does not fall within a predetermined time, for example, a velocity pulse wave out of shape.

According to the present embodiment, on the basis of a period when the area value SDPW has a maximum value, namely, a period when the second area value SDPW2 emerges, it is possible to calculate the number of pulses of the test subject. Accordingly, when the regular data of the velocity pulse wave is detected, in conjunction therewith, it is possible to acquire the number of pulses of the test subject. In addition, since the number of pulses is calculated from the pulse wave waveform whose extreme value is clear, it is possible to obtain the more correct number of pulses. In addition, according to the present embodiment, since the vascular age is estimated from the regular velocity pulse wave data including a feature quantity, it is possible to improve an estimation accuracy.

According to the present embodiment, it is possible to acquire the pulse wave as a velocity signal (velocity pulse wave), using the piezoelectric transducer 10. In addition, since, by only applying the piezoelectric transducer 10 to the skin surface of the test subject, it is possible to acquire the velocity pulse wave, it is possible to acquire the velocity pulse wave (or the pulse wave) simply and with no injury and no pain. Furthermore, since the piezoelectric transducer 10 is compact and inexpensive, it is possible to achieve the improvement of operability and the reduction of cost.

So far, while the embodiment of the present invention has been described, the present invention is not limited to the above-mentioned embodiment but various modifications may occur. For example, while, in the above-mentioned embodiment, the piezoelectric transducer has been used for detecting the pulse wave (velocity pulse wave) of the test subject, an optical pulse wave detection sensor may also be used in place of the piezoelectric transducer, for example.

In addition, a method for extracting the extreme value of the velocity pulse wave is not limited to the above-mentioned embodiment. Furthermore, in place of comparing the extreme value of the velocity pulse wave, a configuration may also be adopted in which the extreme value of an acceleration pulse wave is compared.

REFERENCE SIGNS LIST 1 pulse wave detection device
10 piezoelectric transducer
20 information processing unit
21 amplification unit
22 A/D conversion unit
24 differential waveform acquisition unit
25 area value calculation unit
26 extreme value extraction unit
27 storage unit
28 determination unit
29 vascular age estimation unit
30 number-of-pulses calculation unit

The invention claimed is:
1. A pulse wave detection device comprising:
a pulse wave acquisition unit configured to acquire a pulse wave of a living body;
a velocity pulse wave acquisition unit configured to obtain a velocity pulse wave from the pulse wave acquired by the pulse wave acquisition unit;
an extreme value extraction unit configured to extract an extreme value of the velocity pulse wave acquired by the velocity pulse wave acquisition unit; and
a determination unit configured to (1) compare a previous extreme value and a current extreme value with each other with respect to velocity pulse waves chronologically adjacent to each other and (2) determine that individual velocity pulse waves including the previous and current extreme values are regular velocity pulse waves suitable for analyzing biological information of the living body when a difference between the previous and current extreme values is less than or equal to a predetermined value.

2. The pulse wave detection device according to claim 1, wherein
the extreme value extraction unit chronologically extracts a plurality of extreme values included in the velocity pulse wave that corresponds to one beat of the living body, and
the determination unit determines that the individual velocity pulse waves are the regular velocity pulse waves when respective differences between each of the corresponding plurality of extreme values of previous and current velocity pulse waves are less than or equal to the predetermined value.

3. The pulse wave detection device according to claim 2, wherein
when, from among the plurality of extreme values included in a velocity pulse wave of the one beat, a difference between an earliest extreme value and a final extreme value falls within a predetermined time, the determination unit determines that the velocity pulse wave is the regular velocity pulse wave.

4. The pulse wave detection device according to claim 1, wherein
the extreme value extraction unit extracts a respective extreme value for each velocity pulse wave of at least three successive velocity pulse waves that correspond to at least three beats, respectively, of the living body, and
the determination unit compares the respective extreme values within each of the velocity pulse waves of the at least three successive velocity pulse waves and determines that the at least three successive plurality of velocity pulse waves are regular velocity pulse waves when a difference between each of the respective extreme values in the at least three successive velocity pulse waves is each less than or equal to the predetermined value.

5. The pulse wave detection device according to claim 1, further comprising:
a differential waveform acquisition unit configured to subject the velocity pulse wave acquired by the velocity pulse wave acquisition unit to differential processing and acquire a differential waveform; and
an area value calculation unit configured to obtain an area value of a domain surrounded by the differential waveform acquired by the differential waveform acquisition unit and a reference line, wherein
the determination unit performs the comparison of the previous and current extreme values when the area value obtained by the area value calculation unit is greater than or equal to a predetermined amount.

6. The pulse wave detection device according to claim 5, further comprising:
a number-of-pulses calculation unit configured to calculate a number of pulses of the living body on the basis of a period when the area value acquired by the area value calculation unit has a maximum value.

7. The pulse wave detection device according to claim 1, wherein the pulse wave acquisition unit is a piezoelectric transducer.

8. A pulse wave detection method comprising:
acquiring a pulse wave of a living body using a pulse wave acquisition unit;
using an information processing unit to:
obtain a velocity pulse wave from the pulse wave;
extract an extreme value of the velocity pulse wave;
compare a previous extreme value and a current extreme value with each other with respect to velocity pulse waves chronologically adjacent to each other; and
determine that individual velocity pulse waves including the previous and current extreme values are regular velocity pulse waves when a difference between the previous and current extreme values is less than or equal to a predetermined value; and
using the regular velocity pulse waves to analyze biological information of the living body.

9. The pulse wave detection method according to claim 8, further comprising:
chronologically extracting a plurality of extreme values included in a velocity pulse wave that corresponds to one beat of the living body; and
comparing corresponding extreme values of previous and current velocity pulse waves with each other, respectively, to determine that the individual velocity pulse waves are the regular velocity pulse waves when respective differences between each of the corresponding plurality of extreme values of the previous and current velocity pulse waves are less than or equal to the predetermined value.

10. The pulse wave detection method according to claim 9, wherein
when, from among a plurality of extreme values included in a velocity pulse wave of the one beat, a difference between an earliest extreme value and a final extreme value falls within a predetermined time, it is determined that the velocity pulse wave is the regular velocity pulse wave.

11. The pulse wave detection method according to claim 8, further comprising
extracting a respective extreme value for each velocity pulse wave of at least three successive velocity pulse waves corresponding to at least three beats, respectively, of the living body, and
comparing the respective extreme values within each of the velocity pulse waves of the at least three successive velocity pulse waves with each other, wherein and it is determined that the at least three successive plurality of velocity pulse waves are the regular velocity pulse waves when a difference between each of the respective extreme values in the at least three successive velocity pulse waves is each less than or equal to the predetermined value.

12. The pulse wave detection method according to claim 8, further comprising:
subjecting the velocity pulse wave to differential processing and acquiring a differential waveform; and
obtaining an area value of a domain surrounded by the differential waveform and a reference line, wherein
the comparison of previous and current extreme values is performed when the area value obtained in the area value calculation step is greater than or equal to a predetermined amount.

13. The pulse wave detection method according to claim 12, further comprising:
calculating a number of pulses of the living body on the basis of a period when the area value has a maximum value.

14. The pulse wave detection method according to claim 8, wherein the pulse wave acquisition unit is a piezoelectric transducer.

* * * * *